US005243969A

United States Patent [19]

Jumpertz et al.

[11] Patent Number: 5,243,969

[45] Date of Patent: Sep. 14, 1993

[54] AIR-CLEANING CARTRIDGE WITH AN EXPANDABLE FILM BAG FOR A CHARGE

[75] Inventors: Werner Jumpertz; Werner Sartor, both of Lübeck, Fed. Rep. of Germany

[73] Assignee: Drägerwerk Aktiengesellschaft, Lübeck, Fed. Rep. of Germany

[21] Appl. No.: 868,482

[22] Filed: Apr. 14, 1992

[30] Foreign Application Priority Data

May 25, 1991 [DE] Fed. Rep. of Germany ....... 4117168

[51] Int. Cl.$^5$ .................... A61M 15/00

[52] U.S. Cl. .................... 128/200.24; 128/205.12; 128/205.28

[58] Field of Search .................... 128/201.25, 202.26, 128/205.12, 205.28, 200.24; 206/524.1, 524.5; 53/403, 436, 467, 469

[56] References Cited

U.S. PATENT DOCUMENTS 3,340,671 9/1967 Loo .................... 53/469
3,646,726 3/1972 Hutcheson .................... 53/469
3,978,901 9/1976 Jones .................... 206/524.1
3,982,573 9/1976 Jones .................... 206/524.5
4,632,244 12/1986 Landan .................... 53/403
4,924,919 5/1990 Oyler .................... 53/469
4,974,393 12/1990 Rich et al. .................... 53/469

*Primary Examiner*—Edgar S. Burr
*Assistant Examiner*—Aaron J. Lewis
*Attorney, Agent, or Firm*—McGlew and Tuttle

[57] ABSTRACT

An air-cleaning cartridge for treating respiration air with a chemical as a packing, whose housing wall consists at least partially of an expandable, elastic material, is to be improved such that the size can be increased in a controlled manner prior to filling with the chemical, in order to achieve a reproducible contracting force of the expanded housing and in order to prolong the ready-to-use storage time of the cartridge. To achieve this, a pressure connection 7, through which a compressed gas can be introduced into the housing designed as a film bag 1, 1' in order to expand it to a predetermined volume, can be connected to one of the connections 2. The chemical 5 is filled from the filling chamber 3 into the pressurized, expanded film bag 1. After releasing the internal pressure into the atmosphere, the film bag tightly surrounds the packing introduced on all sides (Figure).

9 Claims, 1 Drawing Sheet

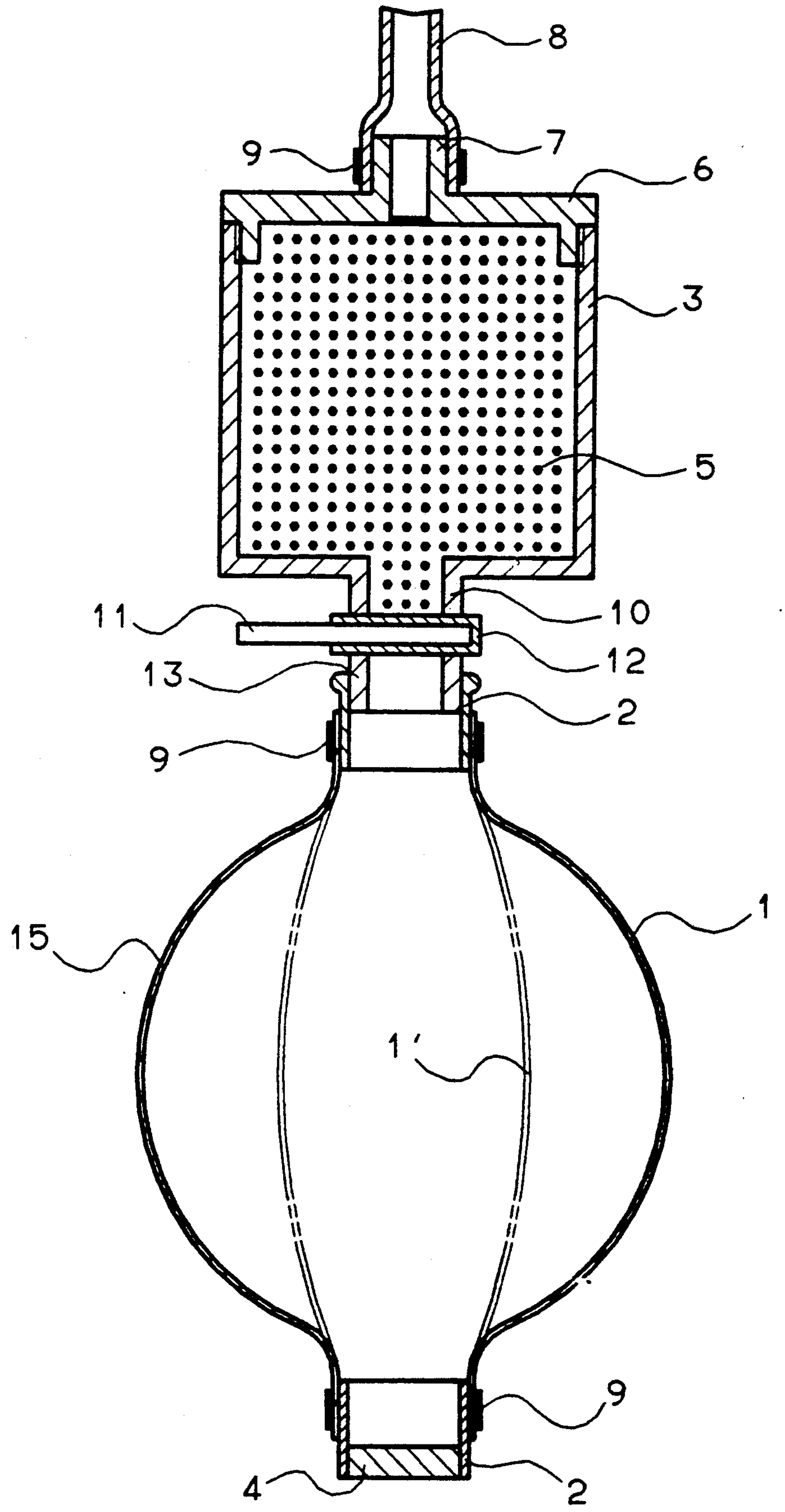
8
9
7
6
3
5
10
11
12
13
2
9
1
15
1'
9
4
2

AIR-CLEANING CARTRIDGE WITH AN EXPANDABLE FILM BAG FOR A CHARGE

FIELD OF THE INVENTION

The present invention pertains to an air-cleaning cartridge for breathing equipment and more particularly to an air-cleaning cartridge with a packing consisting of a granular chemical for treating respiration air in a housing, whose side walls consist at least partially of an expandable, elastic material, and which is provided with one respiration connection each for admitting respiration gas and for removing treated respiration air.

BACKGROUND OF THE INVENTION

Such an air-cleaning cartridge has become known from DE-B 10,96,759. This reference discloses a cylindrical outer wall, which consists of an elastically yielding material, e.g., rubber, provided between the two respiration connections in the prior-art air-cleaning cartridge. The cartridge is filled, while the container is open to the atmosphere, with a granular chemical, which absorbs, e.g., the $CO_2$ present in the exhaled air in a gas mask and breathing equipment in order to again feed the respiration air thus treated to the user of the apparatus. The elastic wall part of the air-cleaning cartridge is expanded by the weight of the packing as the degree of filling progresses, so that the granular packing is subject to the contracting force of the expanded wall part when the cartridge is completely filled. The particles of the packing are held together by this contracting force and packed in a firm unit. The purpose of such a cartridge is to compensate for the reduction of the volume of the packing as a consequence of the expected contracting force during use, so that the flow of the respiration air through the cartridge will take place along the granules of the packing in order to achieve as complete treatment of the respiration air as possible. Otherwise, so-called bypass channels would be formed which would be passed through by the respiration air without flowing past the granules of the packing.

However, it proved to be disadvantageous that the expandability of the elastic housing wall under the intrinsic pressure of the packing is insufficient to keep the packing, whose weight may reach several kg, under a compressing force even during prolonged storage time to the extent that the granules of the packing will remain closely packed, even during a possible transport. When selecting the materials suitable for this purpose, one was limited to materials which were able to accommodate the heavy packing, but consequently did not have sufficient expandability to exert a sufficient contracting pressure, or to materials that were expandable to the extent that an initial contracting pressure was perhaps able to be applied to the granules of the packing after completion of the filling, but whose elasticity decreased during prolonged storage to the extent that even the contracting force dropped to a negligibly low value. In particular, the prior-art expandable air-cleaning cartridge for the above-mentioned reasons is less suitable for receiving especially large packings, which are required in connection with the considerable prolongation of the time of use of the gas masks and breathing equipment in which these air-cleaning cartridges are used. Depending on the variations in the weight of the packing, the prior-art air-cleaning cartridge expands more or less, as a result of which the contracting force thus generated will also assume different values. If one wished to further increase the contracting force in the prior-art filled air-cleaning cartridge it would be necessary to apply a mechanical pressure to the complete packing in order to further expand the wall of the cartridge. However, the application of such a mechanical force would lead to breakage of the granules of the packing, and, as a result, the packing density needed for operation would change. Dust, which settles in the spaces between the granules and increases the flow resistance, is formed due to the fracture on the granules of the chemical.

SUMMARY AND OBJECTS OF THE INVENTION

It is an object of the present invention to improve an air-cleaning cartridge of the above-described type such that the size of the housing can be increased in a controllable manner before the chemical is filled in, in order to achieve reproducible contracting force of the packed housing, and in order to prolong the ready-to-use storage period of the cartridge.

This object is attained in that a pressure connection, through which a compressed gas can be introduced into the housing, which is designed as an isometrically expandable, elastic film bag that can be expanded to several times its original volume, can be connected to one of the connections, and that the granular chemical can be introduced into the inflated film bag, which is put under excess pressure, via a filling connection.

The essential advantage of the present invention is the fact that the housing, designed as a film bag, can now be inflated to a predetermined volume in order to determine in advance a contracting force that can be applied to the subsequent packing, corresponding to the expanding force of the inflated film bag. As a result, the granules of the packing will be compressed with a reproducible compression, and the packing will remain resistant to shaking and remain densely packed even during prolonged storage and during transportation. In addition, the filling process is facilitated by the fact that the film bag is expanded in advance to its final state by introducing compressed air into it until it achieves the desired expansion. The granules of the packing can then be introduced into this expanded film bag via a filling connection.

The filling connection must be sealed against the inflated film bag in a pressure-tight manner, on the one hand, but, on the other hand, it also must permit filling with the chemical. This is advantageously done by connecting the filling connection to a filling chamber, which contains the chemical and can be connected to one of the connections in a pressure-tight manner. One of the connections is thus provided with the pressure connection and the other connection is connected to the filling chamber, in which a sufficient amount of the chemical to be filled in is located. The filling chamber may be closed with a slide at the level of the connection. After the film bag has been inflated via the pressure connection to its desired volume, the chemical is poured from the filling chamber into the expanded film bag, after which the pressure is released, and the expanded film bag will seek to contract, which it is prevented from doing by the completely packed state. The pressure connection and the filling chamber can now be removed from the connections, and the air-cleaning cartridge can be put in place.

It may be advantageous to arrange the pressure connection directly on the filling chamber. A continuous filling unit is thus formed, which can be attached to one of the connections of the cartridge in a pressure-tight manner, and the other connection is sealed. For filling, the compressed gas is passed via the pressure connection into both the filling chamber filled with the chemical and the film bag, after which the film bag will expand, corresponding to its expandability and the filling pressure of the compressed gas, to a volume that is determined by this [expandability and packing pressure], after which the packing can be charged from the filling chamber into the expanded film bag. The pressure of the compressed gas is subsequently released, so that the film bag will contract around the packing.

If the film bag has expanded to the extent that it could hold more packing material than is provided in the filling chamber, a possibility should be provided for filling the film bag repeatedly from the filling chamber. To achieve this, it is favorable to provide the filling connection connected to the filling chamber with a pressure-tight closing slide. This is closed when the filling chamber is empty and is to be filled with more packing material, so that the excess pressure will continue to be present in the as yet incompletely filled film bag.

It was found that a film bag made of an elastomer with a thickness of 0.25 mm is suitable for expanding, in the welded state, from a starting volume of 800 $cm^3$ to a volume of ca. 2500 $cm^3$ under a low pressure of ca. 150 mbar. An elastomer, e.g., polyurethane, welded into a film bag from a film, has a sufficient expandability for obtaining the desired volume, on the one hand, but, on the other hand, it also has sufficient rigidity, so that its contracting force, exerted on the packing, will not decrease over time under the counterpressure of the packing. It is thus possible to expand film bags to five times their original volume.

Since the chemicals needed for the treatment of respiration air are sensitive to moisture, it is advantageous to surround the film bag with a sealing film that is impermeable to water vapor.

The various features of novelty which characterize the invention ar pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWING

In the drawings:

The only Figure is a schematic representation of the air-cleaning cartridge with packing according to the invention.

DETAILED DESCRIPTION OF THE PREFERRED EMBODIMENT

Referring to the drawing in particular, the invention comprises a housing of an air-cleaning cartridge, wherein the housing is designed as a film bag 1 and the air-cleaning cartridge with its connections 2 is connected to a filling chamber 3, on the one hand, and, on the other hand, it is sealed off from the atmosphere by a pressure-tight plug 4. The filling chamber 3 is filled with a granular chemical 5 serving as a packing, and is sealed off from the atmosphere via a cover 6. The cover 6 has a pressure connection 7, which is connected to a compressed gas source (not shown) via a pressure line 8, which is shown only partially. The pressure connection 7 and the connections 2 are sealingly connected to the pressure line 8, on the one hand, and to the film bag 1, on the other hand, by means of clamps. The filling connection 10 of the filling chamber 3 is closed against the film bag 1 in a pressure-tight manner via a slide 11, which can be moved into the open position in a slide guide 12.

Via the pressure connection 7, compressed gas arriving from the pressure line 8 under a pressure of ca. 150 mbar is admitted into the initially empty filling chamber 3, the opened slide 11, and into the film bag 1', which will expand from the nonpressurized shape represented in broken line to the inflated film bag 1 represented in solid line. The slide 11 is then closed, so that the film bag 1 will remain in its inflated form, and the filling chamber 3 can be opened via the cover 6, which can be screwed off, and can be filled with the granular chemical 5. After closing the filling chamber 3 and restoring the pressure connection via the pressure connection 7 and the pressure line 8 to the compressed gas source, the slide 11 is opened, and the contents of the filling chamber 3 will flow into the film bag 1. After it has been completely filled with the granular chemical 5, the pressure can be released from the filling chamber 3 and the film bag 1 into the atmosphere, so that the film bag 1 will seek to contract to its original shape 1' and firmly compress the packing 5 surrounded by it.

Another possibility of filling is to connect the filling chamber, which is filled with the chemical 5, to the compressed gas source (not shown) via the pressure line 8 and the pressure connection 7, while the slide 11, which retains the chemical 5, but allows the compressed gas to flow through, is closed, and to inflate the film bag 1' from its original shape to the inflated form 1 shown. When the slide 11 is opened, the packing 5 of the filling chamber 3 will flow into the expanded film bag 1. Both the filling chamber 3 and the film bag 1 remain under the excess pressure of the compressed gas delivered from the pressure line 8.

To ensure sealing against atmospheric water vapor, the surface of the film bag 1 is provided with a sealing film 15. This sealing film is formed of a material which is impermeable to water.

While a specific embodiment of the invention has been shown and described in detail to illustrate the application of the principles of the invention, it will be understood that the invention may be embodied otherwise without departing from such principles.

What is claimed is:

1. Air-cleaning cartridge with a packing formed of a granular chemical for the treatment of respiration air, the air-cleaning cartridge comprising a housing having side walls formed of an expandable, elastic material, said housing being formed of an isometrically expandable, elastic film bag which can be expanded to several times its original volume, said housing including two respiration connections including a respiration connection for admitting respiration air and a respiration connection for removing treated respiration air; a pressure connection connectable to one of said respiration connections for inflating said film bag to place said film bag under excess pressure; a filling connection connected to one of said respiration connections, said filling connection for introducing the granular chemical into the inflated bag.

2. An air-cleaning cartridge according to claim 1, wherein said filling connection is connected to a filling chamber, said filling chamber containing said granular chemical, said filling chamber being connected to one of said respiration connections in a pressure-type manner.

3. An air-cleaning cartridge according to claim 2, wherein said pressure connection is provided on said filling chamber.

4. An air-cleaning cartridge according to claim 3, wherein said filling connection is provided with a pressure-type closing slide.

5. An air-cleaning cartridge according to claim 1, wherein said film bag is formed of an elastomer with a thickness substantially equal to 0.25 mm.

6. An air-cleaning cartridge according to claim 1, wherein said film bag is surrounded by a sealing film that is impermeable to water vapor.

7. A method of filling an air-cleaning cartridge, comprising: providing a housing with side walls formed of an isometrically expandable, elastic film bag which may be expanded to several times its original volume, the housing having two respiration connections including a respiration connection for admitting respiration air and a respiration connection for removing treated respiration air; providing a pressure connection to one of said respiration connections to inflate said elastic film bag to place said elastic film bag under excess pressure; and connecting a filling connection to one of said respiration connections and introducing a granular chemical into said housing via said filling connection.

8. A method according to claim 7, wherein said filling connection is connected to a filling chamber, said filling chamber being filled with said granular chemical and connected to one of said respiration connections in a pressure type manner.

9. A method according to claim 8, wherein said pressure connections is provided connected to said filling chamber.

* * * * *